(12) United States Patent
Konishi

(10) Patent No.: US 10,585,045 B2
(45) Date of Patent: Mar. 10, 2020

(54) INSPECTING DEVICE, INSPECTING METHOD, AND PROGRAM

(71) Applicant: OMRON Corporation, Kyoto-shi, Kyoto (JP)

(72) Inventor: Yoshinori Konishi, Kyoto (JP)

(73) Assignee: OMRON Corporation, Kyoto-shi (JP)

(*) Notice: Subject to any disclaimer, the term of this patent is extended or adjusted under 35 U.S.C. 154(b) by 0 days.

(21) Appl. No.: 16/339,510

(22) PCT Filed: Oct. 26, 2017

(86) PCT No.: PCT/JP2017/038687
§ 371 (c)(1),
(2) Date: Apr. 4, 2019

(87) PCT Pub. No.: WO2018/110112
PCT Pub. Date: Jun. 21, 2018

(65) Prior Publication Data
US 2019/0285554 A1    Sep. 19, 2019

(30) Foreign Application Priority Data
Dec. 15, 2016 (JP) .................... 2016-243248

(51) Int. Cl.
*G01N 21/88* (2006.01)
*G01J 1/44* (2006.01)
(Continued)

(52) U.S. Cl.
CPC ............ *G01N 21/8851* (2013.01); *F21S 2/00* (2013.01); *G01J 1/44* (2013.01); *G01M 11/00* (2013.01);
(Continued)

(58) Field of Classification Search
CPC .............. G01N 21/3504; G01N 21/359; G01N 21/4788; G01N 21/8806; G01N 21/9501;
(Continued)

(56) References Cited

U.S. PATENT DOCUMENTS

| 2009/0015825 A1 | 1/2009 | Chung |
| 2013/0033595 A1* | 2/2013 | Adelson ............... A61B 5/0077 348/92 |

(Continued)

FOREIGN PATENT DOCUMENTS

| CN | 102435618 A | 5/2012 |
| CN | 106054309 A | 10/2016 |

(Continued)

OTHER PUBLICATIONS

An English translation of the International Search Report("ISR") of PCT/JP2017/038687 dated Nov. 28, 2017.

(Continued)

*Primary Examiner* — Michael P Stafira
(74) *Attorney, Agent, or Firm* — Metrolex IP Law Group, PLLC

(57) ABSTRACT

An inspecting device includes: an image acquiring unit which acquires a light-emitting surface image as a photographed image of the light-emitting surface; an inspecting unit which sets an inspecting range in a position of the light-emitting surface image in which the failure may appear, detects, from the inspecting range, a bright region which is brighter than a lower limit threshold value, calculates an evaluation value evaluating both the size and luminance of the bright region, and determines the presence or absence of the failure on the basis of the evaluation value; and an output unit which outputs information obtained by the inspecting unit.

13 Claims, 9 Drawing Sheets

(51) Int. Cl.
*G02F 1/13* (2006.01)
*G06T 7/00* (2017.01)
*G06T 1/00* (2006.01)
*G01M 11/00* (2006.01)
*F21S 2/00* (2016.01)

(52) U.S. Cl.
CPC .............. *G02F 1/13* (2013.01); *G02F 1/1309* (2013.01); *G06T 1/00* (2013.01); *G06T 7/0008* (2013.01); *G06T 2207/30108* (2013.01)

(58) Field of Classification Search
CPC ............ G01N 2201/101; G01N 29/00; G01N 33/0036; G01N 33/225; G01N 33/4925; G01N 35/00871; G02B 27/017; G02B 1/06; G02B 2005/1804; G02B 2027/0181; G02B 26/023; G02B 26/0858; G02B 26/10; G02B 27/0093; G02B 27/0172; G02B 27/0179; G02B 5/0278; G02B 5/0284; G02B 5/205; G02B 5/22; G01J 1/0407; G01J 1/0418; G01J 1/26; G01J 1/429; G01J 2003/1213; G01J 2003/1221; G01J 2003/2806; G01J 2003/2826; G01J 3/0208; G01J 3/021; G01J 3/06; G01J 3/10; G01J 3/2803; G01J 3/2823; G01J 3/42

See application file for complete search history.

(56) References Cited

U.S. PATENT DOCUMENTS

| | | | |
|---|---|---|---|
| 2015/0253487 A1* | 9/2015 | Nichol | ................. G02B 6/0036 362/610 |
| 2016/0313494 A1* | 10/2016 | Hamilton | ............. G02B 6/0068 |
| 2018/0059479 A1* | 3/2018 | Ogura | .................... G02B 6/005 |

FOREIGN PATENT DOCUMENTS

| | | |
|---|---|---|
| JP | 2005-207808 A | 8/2005 |
| JP | 2007-172397 A | 7/2007 |
| JP | 2015-042942 A | 3/2015 |
| TW | I226959 B | 1/2005 |

OTHER PUBLICATIONS

An English translation of the Written Opinion("WO") of PCT/JP2017/038687 dated Nov. 28, 2017.

* cited by examiner

INSPECTING DEVICE, INSPECTING METHOD, AND PROGRAM

TECHNICAL FIELD

The present invention relates to a technique for inspecting for a failure in an edge-lit type plane light source device.

BACKGROUND ART

An edge-lit type plane light source device is used as a backlight for a liquid crystal display device. The edge-lit type device includes light sources such as LEDs (Light Emitting Diodes) along an edge of the light-emitting surface of the plane light source device and is configured to guide light emitted from the light sources to the light-emitting surface by a plate-shaped light guide (called a light-guiding panel). The edge-lit type plane light source device can be relatively easily reduced in size/thickness and therefore has been widely used in small size electronic equipment such as a smart phone.

An edge-lit plane light source device may be encountered with a failure related to luminance unevenness attributable to various causes such as a defect in a mold for a light-guiding panel or poor molding thereof and shifting during assembly. One such failure is an extremely brighter part than standard luminance appearing at an end excluding a part provided with light sources. (Herein, the failure of this kind will be referred to as a "bright edge".)

At present, inspection of failures of this kind actually depends on visual sensory inspection carried out by a person (an inspector). Therefore, the inspection procedure may take time and trouble and can be costly or the results of the inspection depend much on personal skills, and there has been a demand for automation and objectification (quantification) of the inspection.

Note that PTL 1 proposes a method for automatically inspecting a liquid crystal panel for luminance unevenness (referred to as a "spot defect" in the document) by image processing though the document does not concern inspection of a plane light source device. However, when the inventor attempted to apply the method disclosed in the document to inspection of a bright edge, the result was not comparable with human sensory inspection.

CITATION LIST

Patent Literature

PTL 1: Japanese Patent Application Publication No. 2007-172397

SUMMARY OF INVENTION

Technical Problem

With the foregoing in view, it is an object of the present invention to provide a technique for objectively and automatically inspecting for a failure related to luminance unevenness generated in an edge-lit type plane light source device.

Solution to Problem

According to the present invention, in order to achieve the object, a new evaluation value (an evaluation index) for quantifying the occurrence degree of a bright edge is introduced. With an algorithm proposed according to the present invention, an evaluation value can be automatically calculated from a photographed image of a light-emitting surface of a plane light source device, and bright edge inspection can be carried out automatically on the basis of the evaluation value.

More specifically, an inspecting device according to a first aspect of the present invention inspects for a failure related to luminance unevenness in a light-emitting surface of a plane light source device, the plane light source device is an edge-lit type plane light source device having a light source arranged along one side of the light-emitting surface and a light-guiding panel which guides light emitted from the light source to the light-emitting surface, the failure is a part brighter than reference luminance appearing at an end of the light-emitting surface excluding a part provided with the light source, and the inspecting device includes an image acquiring unit which acquires a light-emitting surface image as a photographed image of the light-emitting surface, an inspecting unit which sets an inspecting range in a position of the light-emitting surface image in which the failure may appear, detects, from the inspecting range, a bright region which is brighter than a lower limit threshold value, calculates an evaluation value evaluating both the size and luminance of the bright region, and determines the presence or absence of the failure on the basis of the evaluation value, and an output unit which outputs information obtained by the inspecting unit.

According to the configuration, an evaluation value representing the occurrence degree of a bright edge is calculated on the basis of a photographed image of the light-emitting surface of the plane light source device, and the presence/absence of a bright edge can be determined on the basis of the evaluation value. Therefore, objective and automatic inspection for bright edges may be performed. Furthermore, since an evaluation value for evaluating both the size and luminance of a bright region is used, a result comparable with the conventional sensory inspection (human visual inspection) can be obtained.

When the bright region includes a part brighter than an upper threshold value, the inspecting unit may evaluate the part brighter than the upper limit threshold value lower than actual luminance thereof in calculating the evaluation value. For example, when the bright region includes a part brighter than the upper limit threshold value in the bright region, the inspecting unit may treat the luminance of the part brighter than the upper limit threshold value as being equal to the upper limit threshold value in calculating the evaluation value.

The bright edge has a locally extremely bright spot in some cases. In this case, if the luminance of the spot is directly reflected on an evaluation value, the evaluation value could be excessive and differ materially from the result of human sensory inspection. Therefore, according to the present invention, the upper limit threshold value is set so that the influence of the luminance of a part brighter than the upper limit threshold value upon the evaluation value is reduced, so that an appropriate evaluation value (close to that obtained in human sensory inspection) can be obtained even if there is an extremely bright spot.

The light-emitting surface image may be a rectangular image having a side parallel to a first direction and a side parallel to a second direction, and when the failure appears along a side parallel to the second direction, the inspecting unit may produce a one-dimensional luminance profile representing change in a luminance value in the first direction in the inspecting range and detect, as the bright region, a range in the luminance profile in the first direction in which the luminance value exceeds the lower limit threshold value, and calculate, as the evaluation value, the area of a closed region surrounded by the luminance profile in the bright region, two straight lines representing the range of the bright region in the first direction, a straight line representing reference luminance, and a straight line representing the upper limit threshold value.

Here, the "range of the bright region in the first direction" corresponds to the size of the bright region, the width between the "straight line representing reference luminance" and the "luminance profile" and the width between the "straight line representing the reference luminance" and the "straight line representing the upper limit threshold value" correspond to the luminance of the bright region (the luminance difference from the reference luminance). Therefore, the area of the closed region corresponds to one of the evaluation values for evaluating both the size and luminance of the bright region. Using the area of the closed region as the evaluation value, an appropriate evaluation value can be obtained by simple calculation.

The reference luminance may be a minimum luminance value in the luminance profile in the inspecting range. A person easily perceives relative luminance change in a local region as luminance unevenness. Therefore, when the reference luminance is set on the basis of the minimum luminance in the inspecting range, local luminance unevenness (or within the inspecting range) can be evaluated as appropriate.

The lower limit threshold value and the upper limit threshold value may be set on the basis of the reference luminance. When the lower limit threshold value is set to a value about 1.025 times as large as the reference luminance, while for example the upper limit threshold value is set to a value about 1.15 times as large as the reference luminance, an evaluation value very close to that obtained by human sensory inspection can be obtained.

The width of the inspecting range in the second direction may be smaller than the width of the light-emitting surface image in the second direction. This is because a bright edge sometimes appears only at a part of the width of the light-emitting surface image in the second direction.

The output unit may output the evaluation value and a result of determination on the presence or absence of a failure. Using the output of the result of determination, the presence/absence of a bright edge or whether the plane light source device is good or defective can be immediately determined. The evaluation value is also output, and therefore the reason for the result of determination can be checked, so that convincingness and objectivity about the result of determination may improve.

The output unit may output an image obtained by superposing the light-emitting surface image or an image obtained by processing the light-emitting surface image with information indicating a position in which the failure appears. The output of the superposed image allows the location of interest in which a bright edge appears to be grasped intuitively and easily, which is also useful in checking the actual product.

The output unit may output a luminance profile in the inspecting range. The output of the luminance profile allows the size of the bright region or the luminance difference from the reference luminance to be grasped.

Note that the present invention may be implemented as an inspecting device or a bright edge quantifying device having at least a part of the described configuration and functions. The present invention may be implemented as an inspecting method, a control method for the inspecting device, or a bright edge quantifying method including at least part of the above processing; a program which allows a computer to execute any of the methods; or a computer-readable recording medium which records the program in a non-transitory manner. The present invention may be implemented by combining parts of the configuration and the processing unless any technical discrepancy arises.

Advantageous Effects of Invention

According to the present invention, a failure related to luminance unevenness generated in an edge-lit type plane light source device can be inspected automatically and objectively.

DESCRIPTION OF EMBODIMENTS

The processing concerns a technique for objectively (quantitatively) evaluating the presence or absence of a failure called a bright edge generated in an edge-lit type plane light source device and automatically inspecting for the presence/absence of a bright edge. The inspecting technique can be preferably applied to in-line inspection in the final process in a manufacturing line for a plane light source device or acceptance inspection for a part (a plane light source device) by a manufacturer of a product which includes a plane light source device. Note that in the following description of the embodiment, the plane light source device is a backlight used in a liquid crystal display device by way of illustration, while the present invention may be applied to inspection of a plane light source device for any other use such as a lighting device and a digital signage device.

Hereinafter, a preferred embodiment of the present invention will be described with reference to the drawings. Note however that the configuration and operation of a device disclosed in the following description of the embodiment are described by way of illustration, and the same is not intended to limit the scope of the present invention.

(Plane Light Source Device)

Figure 1:
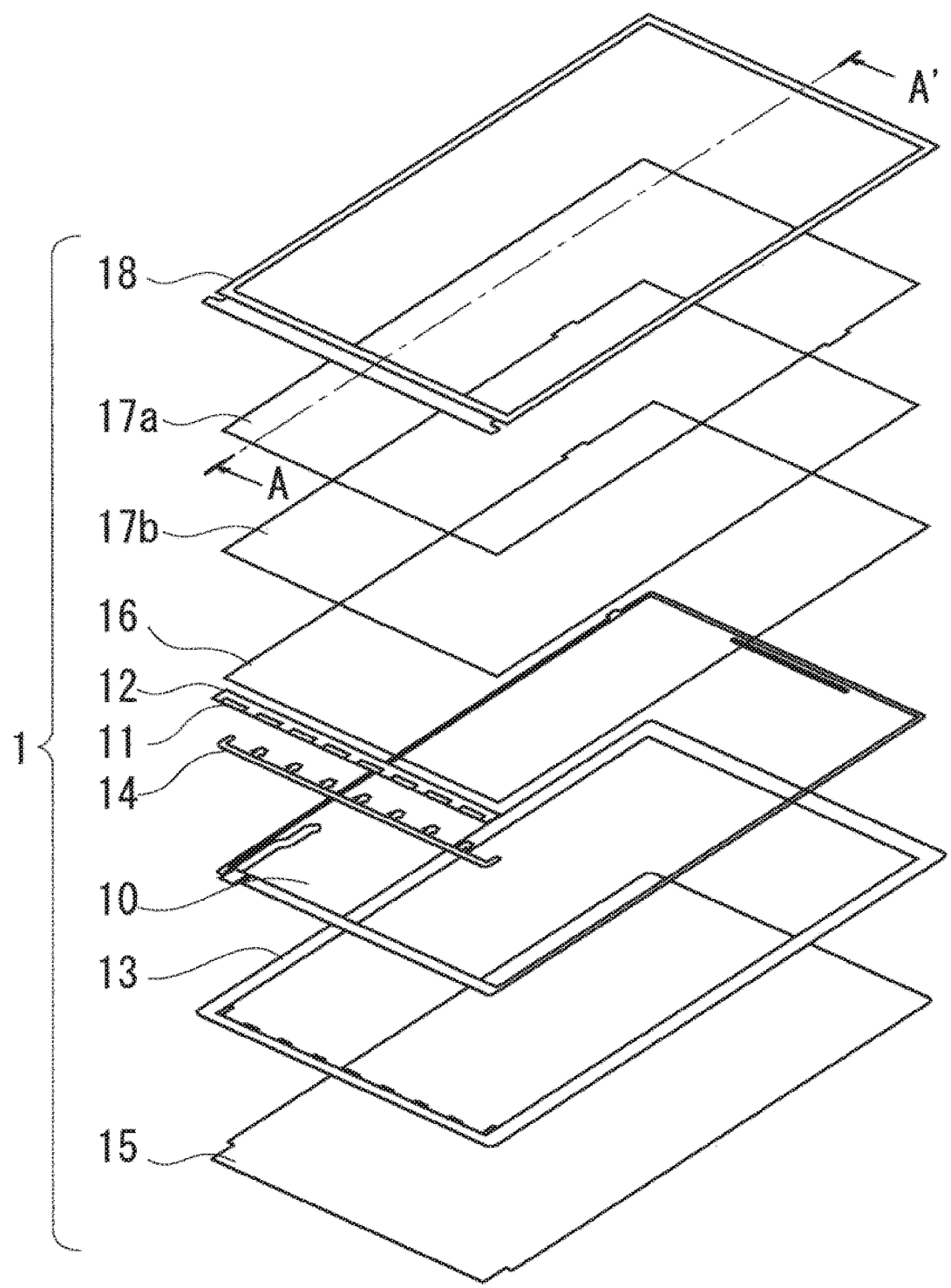
FIG. 1 is a perspective view illustrating the basic structure of a plane light source device.

FIG. 1 is a perspective view illustrating the basic configuration of a plane light source device 1. The plane light source device 1 includes a light-guiding panel (a light guide) 10, multiple light sources 11, a flexible printed circuit board (hereinafter as the "FPC") 12, a frame 13, and a fixing member 14. The plane light source device 1 further includes a reflecting sheet 15 provided on the lower surface side of the light-guiding panel 10. The plane light source device 1 includes a diffusion sheet 16, prism sheets 17a and 17b, and a light-shielding sheet 18 layered upon each other on the upper surface side of the light-guiding panel 10.

The light-guiding panel 10 has a substantially plate shape and is made of a translucent material such as a polycarbonate resin and a polymethyl methacrylate resin. The upper surface of the light-guiding panel 10 serves as a light-emitting surface (also referred to as a "light exit surface") from which light is emitted. The light-guiding panel 10 guides light introduced into the light-guiding panel 10 from the light sources 11 to the light emitting surface using total reflection, so that the entire light-emitting surface lights substantially uniformly.

The light source 11 is for example an LED light source which emits white light. Note however that the light source may be an LED light source other than a white LED light source or a light source other than an LED light source or may include light sources in multiple colors (such as RGB). The light source 11 is mounted to the FPC 12 and supplied with electric power from the FPC 12 to be driven. According to the embodiment, eight light sources 11 are aligned in a line at equal intervals along a short side (referred to as a "first side") of the light-emitting surface of the light-guiding panel 10.

The frame 13 is a member having an opening and a frame shape consisting of four sides. The frame 13 is made for example of a polycarbonate resin containing titanium oxide. The light-guiding panel 10 is fitted to the frame 13, and the inner peripheral surface of the frame 13 surrounds side surfaces which form the outer peripheral surface of the light-guiding panel 10. The frame 13 has a high reflectance and reflects light so that light in the light-guiding panel 10 does not leak from the outer peripheral surface of the light-guiding panel 10. A storing part for storing the light sources 11 is provided at one side of the frame 13, and the storing part is provided with a reflecting wall which reflects light from the light sources 11.

The fixing member 14 is provided for example at the lower surface of the FPC 12 to fix the FPC 12, the frame 13, and the light-guiding panel 10. The fixing member 14 is for example a length of double-side adhesive tape having upper and lower adhesive surfaces but it may be any other material. The reflecting sheet 15 is a flat and smooth sheet of a white resin sheet or a metal foil with a high reflectance and reflects light so that light inside the light-guiding panel 10 does not leak from the lower surface of the light-guiding panel 10. The diffusion sheet 16 is a translucent resin film and diffuses light emitted from the light-emitting surface of the light-guiding panel 10 so that the directivity of the light is increased. The prism sheets 17a and 17b are each a transparent resin film provided with a very fine triangular prism-shaped pattern on the upper surface thereof, collect light diffused by the diffusion sheet 16, and increases the luminance when the plane light source device 1 is seen from the upper surface side. The light-shielding sheet 18 is a black adhesive sheet having upper and lower adhesive surfaces. The light-shielding sheet 18 is frame-shaped and reduces light leakage.

(Bright Edge)

Figure 2A:
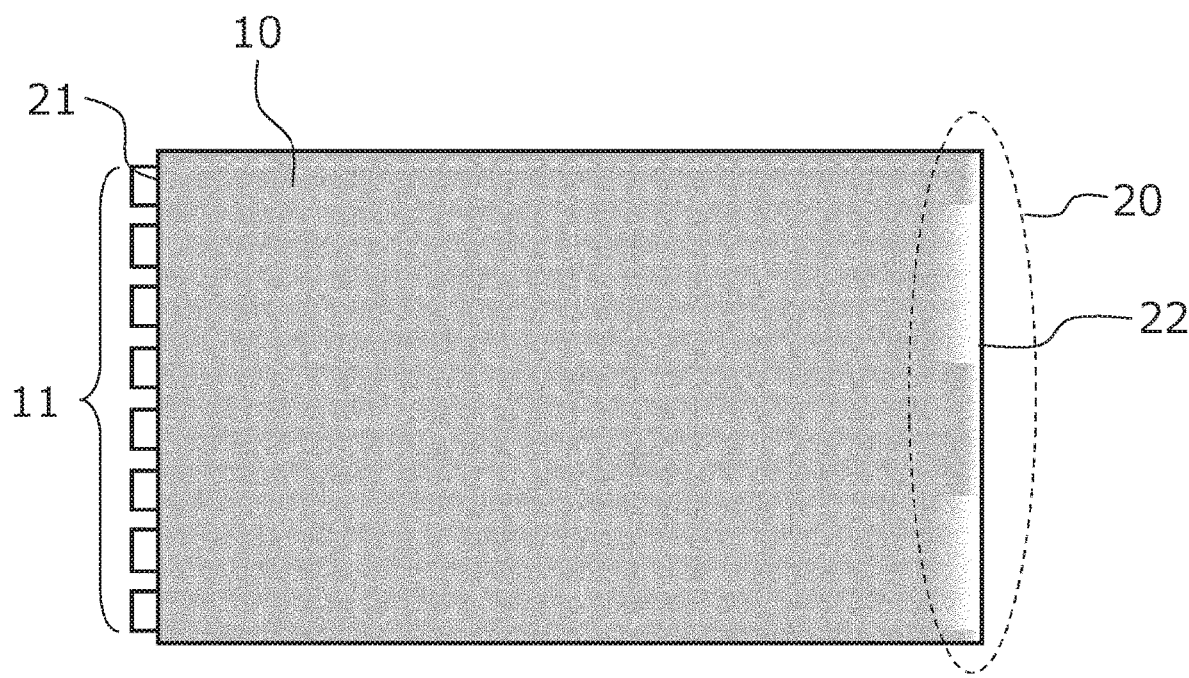
FIGS. 2A and 2B are views illustrating an example of a bright edge.
Figure 2B:
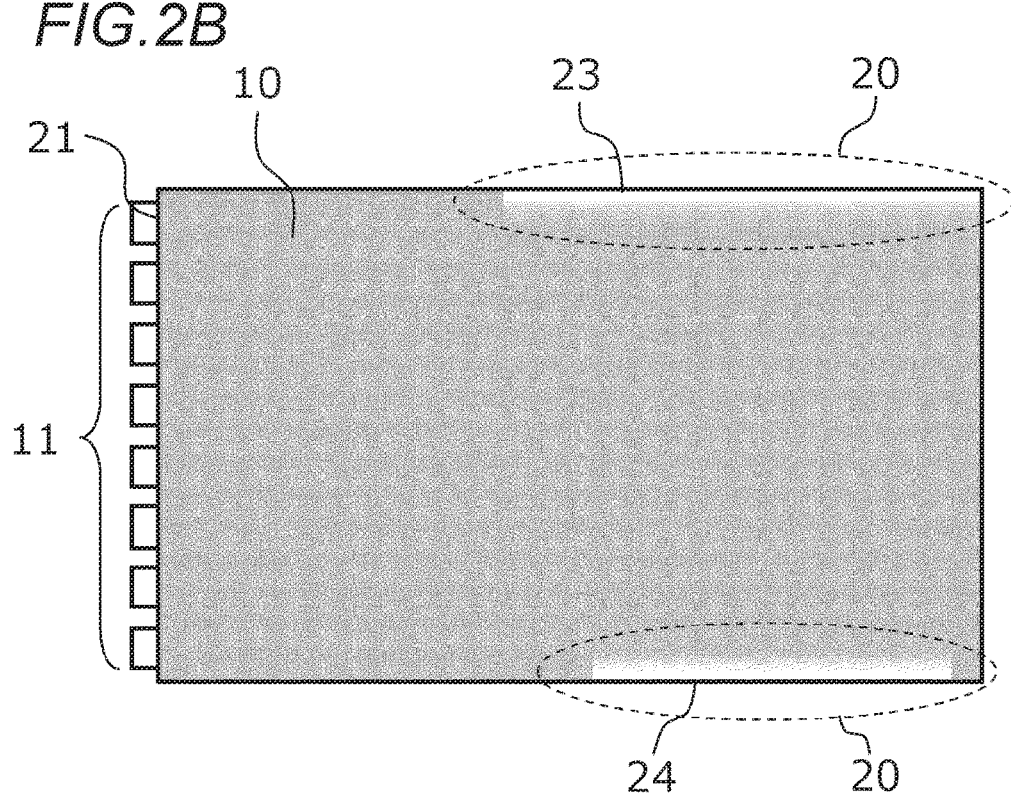

The edge-lit type plane light source device illustrated in FIG. 1 may be encountered with a failure related to luminance unevenness attributable to various causes such as a defect in a mold for the light-guiding panel 10 or poor molding thereof, and shifting during assembly of various components, and shifting in adhering sheets 15 to 18 together. In one such failure called the "bright edge," an extremely brighter part than standard luminance appears at an end excluding a part provided with light sources 11. The bright edge is caused when light entered from the light sources 11 into the light-guiding panel 10 is not completely let out to the light-emitting surface and reaches an end of the light-guiding panel 10, and one of the most frequently occurring failures. As shown in FIG. 2A, a bright edge 20 may appear along a side 22 opposed to a side (a first side) 21 provided with the light sources 11 in some cases, while as shown in FIG. 2B, the bright edge 20 may appear along sides 23 and 24 that are orthogonal to the side 21 provided with the light sources 11 in other cases. Note that the light-guiding panel may have a shape other than the rectangular shape (such as a circular shape, an elliptical shape, a polygonal shape, and an asymmetric shape), and the bright edge can be generated at an end excluding the part (or the part to which light from the light sources is entered) provided with the light sources regardless of the shape of the light-guiding panel.

In creating a quantifying algorithm for a bright edge and automating the inspection, the inventor has analyzed a conventional sensory inspection procedure and inspection results and gained the following findings.

(1) An inspector focuses on a region significantly brighter than the surrounding region (hereinafter as the "bright region"). The inspector dismisses a region only slightly brighter than the surrounding region because luminance unevenness is not noticeable.

(2) The inspector often determines that luminance unevenness is more noticeable as the area of the bright region is greater.

(3) The inspector determines that luminance unevenness is more noticeable as the luminance difference between the bright region and the surrounding region is greater. Note however that when the luminance difference exceeds a certain level, the degree of luminance unevenness perceived by the inspector is barely different.

According to the findings, the inventor has designed an evaluation value (referred to as a "bright edge evaluation value") evaluating both the size and luminance of a bright region and quantified the occurrence degree of a bright edge on the basis of the evaluation value. The evaluation value evaluating both the size and luminance of a bright region means that the evaluation value depends both on the size and luminance of the bright region or has a positive correlation to both the size and luminance of the bright region. The introduction of the evaluation value allows the bright edge occurrence degree to be understood quantitatively and objectively, so that the bright edge inspection which would otherwise be dependent on conventional sensory inspection can be automated.

Hereinafter, a specific example of the bright edge evaluation value and inspecting processing using the value will be described in detail.

(Inspecting Device)

Figure 3:
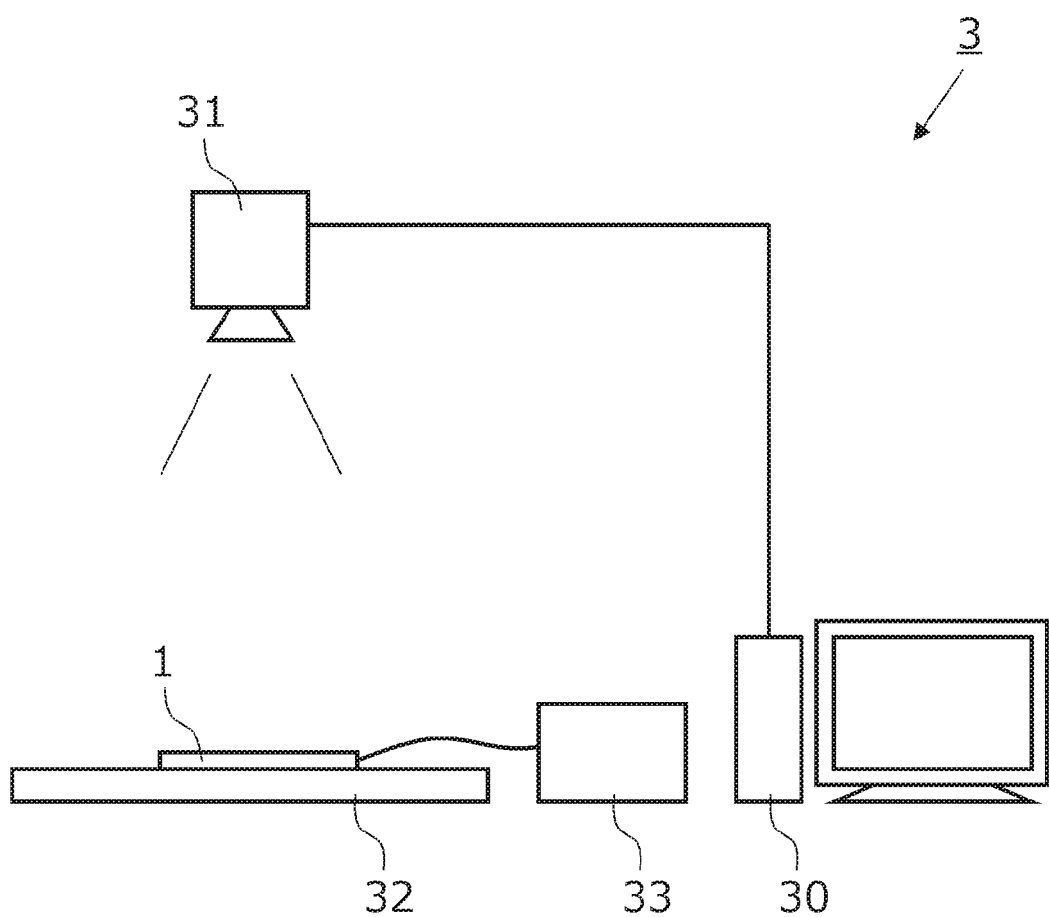
FIG. 3 is a view illustrating the hardware configuration of an inspecting device.

With referring to FIG. 3, the structure of an inspecting device 3 according to an embodiment of the present invention will be described. FIG. 3 illustrates the hardware configuration of the inspecting device 3. The inspecting device 3 evaluates a bright edge occurrence degree in a plane light source device 1 quantitatively and automatically and determines the presence or absence of a bright edge which should be removed as a defect.

As shown in FIG. 3, the inspecting device 3 substantially includes an information processing device (computer) 30, an imaging device 31, a stage 32, and a constant current power source 33. The information processing device 30 includes a general-purpose or dedicated computer which has a CPU (central processing unit) as a hardware processor, a memory as a main storage, a storage device for storing programs or data in a non-transitory manner (such as a hard disk and a flash memory), an input device (such as a mouse device, a keyboard, and a touch panel), a display device, an interface with the imaging device 31, and a network interface.

The imaging device 31 is a device which photographs the plane light source device 1 placed on the stage 32 and outputs a digital image. The imaging device 31 may be an optical system, an imaging element, or a digital camera which has an interface with the information processing device 30. Since the process is for the purpose of measuring the luminance of the plane light source device 1, the camera may be a monochrome camera if the plane light source device 1 is a monochromatic light source, and the camera is preferably a color camera if the plane light source device 1 is a multi-color light source device. The plane light source device 1 to be inspected is placed on the stage 32. The constant current power source 33 is a device which supplies the plane light source device 1 with electric power. Although not shown, the imaging device 31 and the stage 32 may be provided in a clean bench.

The size (the length and width) of the light-emitting surface or the light emission luminance may be different among different models of the plane light source devices 1. Therefore, depending on the size of the light-emitting surface to be inspected, the distance between the stage 32 and the imaging device 31 or the zoom of the imaging device 31 is preferably adjusted, so that the relation between one pixel of an image obtained by the imaging device 31 and an actual size on the light emitting surface is calibrated. The average luminance of an image obtained by the imaging device 31 is preferably calibrated by adjusting the exposure time of the imaging device 31 depending on the light emitting luminance of the test object. These kinds of calibration may be carried out automatically by the information processing device 30 or manually by an operator.

Figure 4:
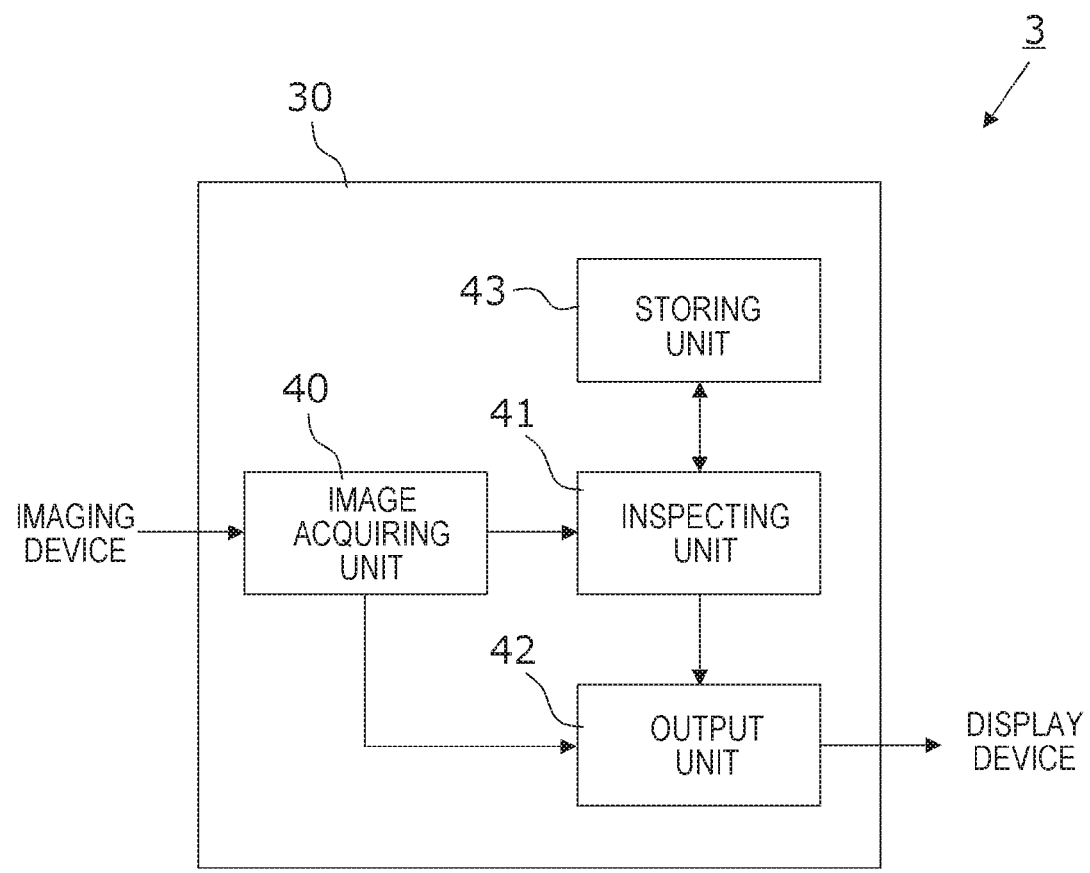
FIG. 4 is a block diagram illustrating functions related to bright edge inspecting processing by the inspecting device.

FIG. 4 is a block diagram showing functions related to bright edge inspecting processing by the inspecting device 3. The inspecting device 3 includes an image acquiring unit 40, an inspecting unit 41, an output unit 42, and a storing unit 43. The image acquiring unit 40 represents the function of obtaining image data acquired by photographing the plane light source device 1 for inspection from the imaging device 31. The inspecting unit 41 represents the function of analyzing the image data acquired by the image acquiring unit 40 and inspecting the presence or absence of a bright edge. The output unit 42 represents the function of outputting image data and information such as a result of inspection to the display device. The storing unit 43 represents the function of storing setting data such as thresholds used for inspection processing. These functions will be described in detail.

The function shown in FIG. 4 is basically implemented as the CPU of the information processing device 30 loads necessary programs from the storage device and executes the programs. Note however that one or all of the functions may be substituted by a circuit such as an ASIC and an FPGA. One or all of these functions may be executed by another computer by using cloud computing or distributed computing techniques.

(Inspecting Processing)

Figure 5:
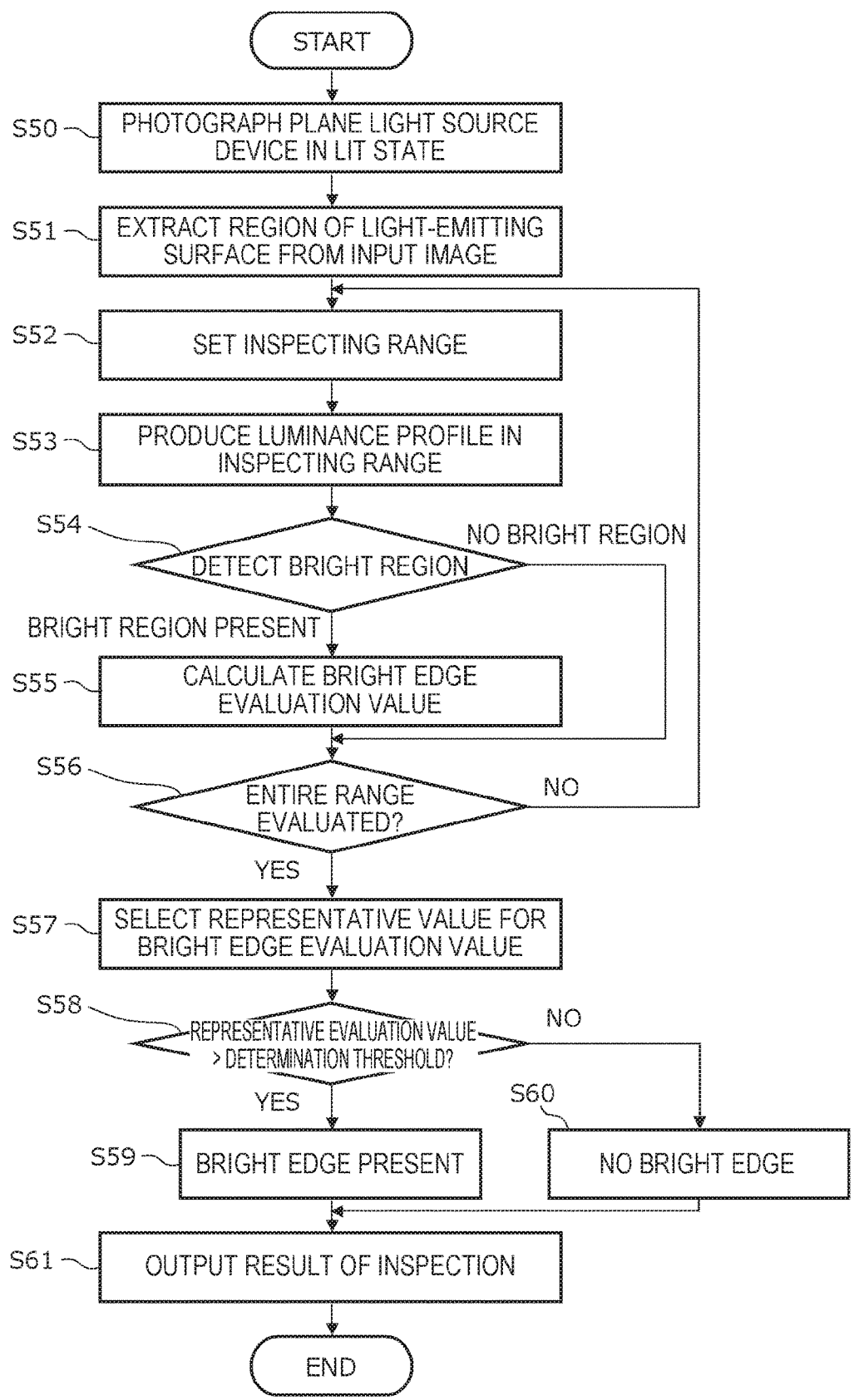
FIG. 5 is a flowchart for illustrating bright edge inspecting processing by the inspecting device.

With reference to FIG. 5, the flow of bright edge inspecting processing will be described. FIG. 5 is a flowchart for illustrating the bright edge inspecting processing by the inspecting device 3.

To start with, an inspector places the plane light source device 1 on the stage 32 in a prescribed position so that the light-emitting surface faces the side of the imaging device 31. The plane light source device 1 is connected to the constant current power source 33 to drive the light sources 11, and the plane light source device 1 is lit. Note that the test object is provided manually in the inspecting device 3 according to the embodiment, while operation such as introduction, positioning, and connection with the power source, and withdrawal of the test object may be automated.

In step S50, the imaging device 31 photographs the plane light source device 1 in the lit state, and the image acquiring unit 40 takes in image data from the imaging device 31. The resolution of the image is arbitrary while according to the embodiment, the image has a resolution of about 0.1 mm (an actual size on the light-emitting surface) per pixel.

Figure 6B:
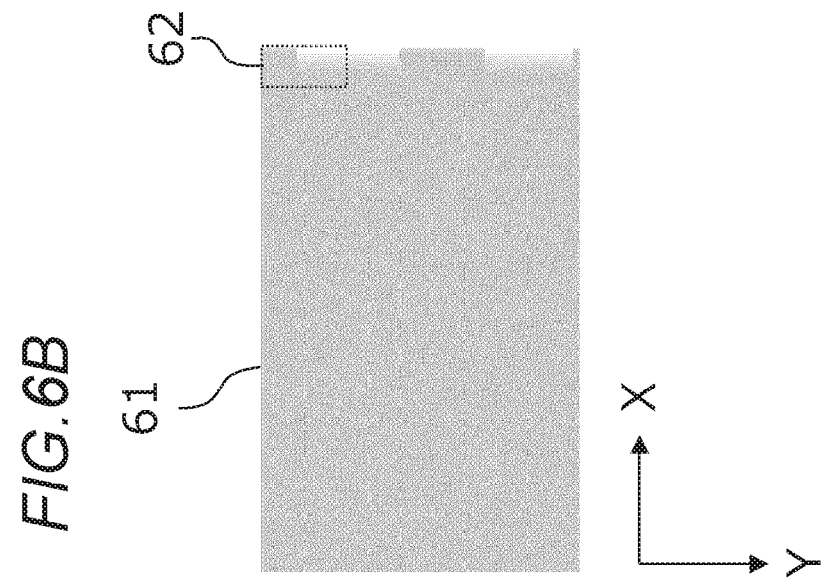
FIG. 6B is a view of an example of a light-emitting surface image extracted from the input image.
Figure 6A:
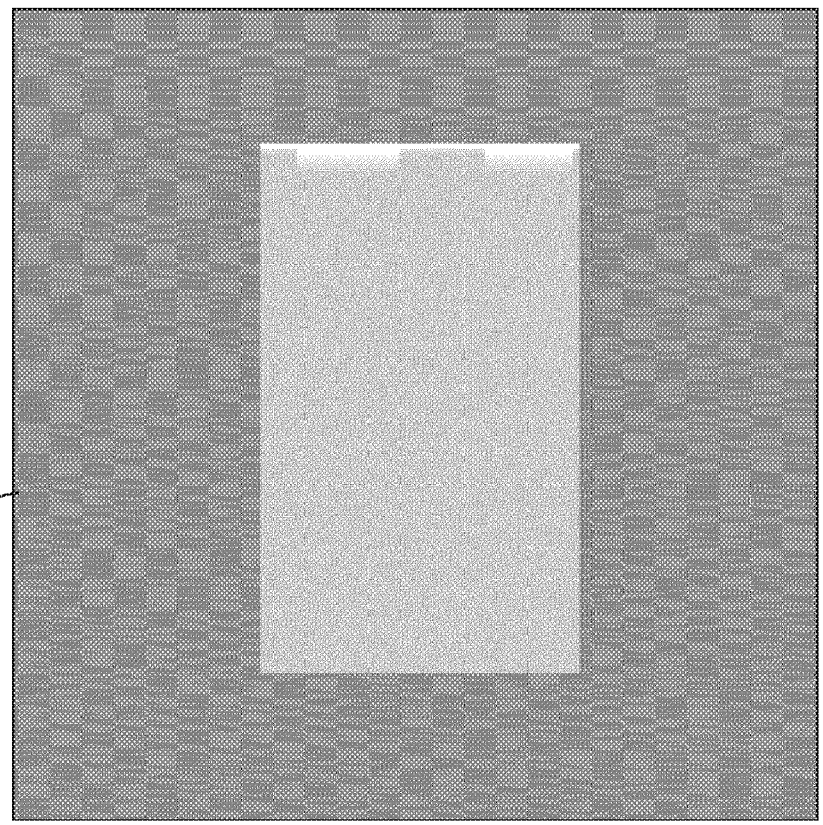
FIG. 6A is a view of an example of an input image.

In step S51, the image acquiring unit 40 extracts only the region of the light-emitting surface from the input image taken in step S50. Hereinafter, the image of the extracted region of the light-emitting surface will be referred to as a light-emitting surface image. FIG. 6A illustrates an example of an input image 60, and FIG. 6B illustrates an example of the light-emitting surface image 61 extracted from the input image 60. According to the embodiment, the light-emitting surface image 61 is generated so that the long sides of the light-emitting surface are parallel with the X-axis of the image.

The light-emitting surface region may be extracted by any method. For example, the image acquiring unit 40 may (1) binarize the original image, (2) remove noises in the background region (the region other than the light-emitting surface) by closing processing, and then (3) extract the contour of the light-emitting surface. Furthermore, when the contour of the light-emitting surface is inclined with respect to the image coordinate system, inclination correction (rotational correction) may be carried out. Alternatively, if the test object is positioned sufficiently accurately on the stage, it may only be necessary to cut a prescribed range from the original image.

Then, the inspecting unit 41 inspects the light-emitting surface image 61. According to the embodiment, a bright edge which appears along a side parallel to the Y-direction of the light-emitting surface image as shown in FIG. 6B is subject to inspection. (In other words, the X-direction corresponds to the "first direction" according to the present invention and the Y-direction corresponds to the "second direction" according to the present invention.)

To start with, in step S52, the inspecting unit 41 sets an inspecting range (also referred to as a window) to the light-emitting surface image 61. The inspecting range is a local area used for failure detection and evaluation calculation and set in a position in the light-emitting surface image 61 in which a failure may appear. In the example shown in FIG. 6B, the inspecting range 62 may be set along the right end of the light-emitting surface image 61 since the light sources are provided on the left side of the light-emitting surface image 61. Hereinafter, an exemplary case in which the inspecting range 62 in a square having an X-width of 100 pixels (which corresponds to about 10 mm) and a Y-width of 200 pixels (which corresponds to about 20 mm) will be described. Note however that the size and shape of the inspecting range 62 are arbitrary and may be designed, as appropriate, according to the size of the light-emitting surface of a test object or the bright edge appearing range.

Figure 7A:
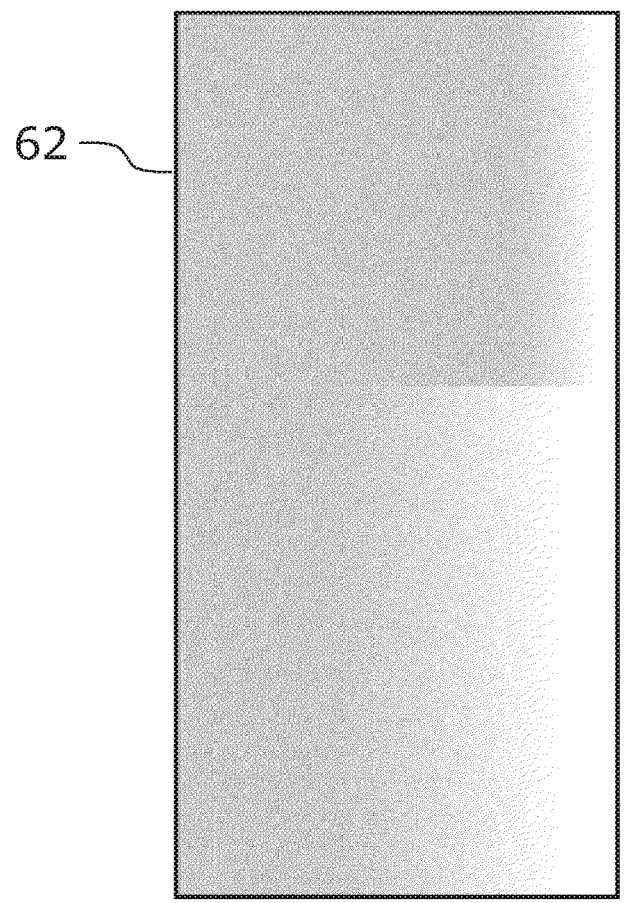
FIG. 7A is a view of an example of an image in an inspecting range.
Figure 7B:
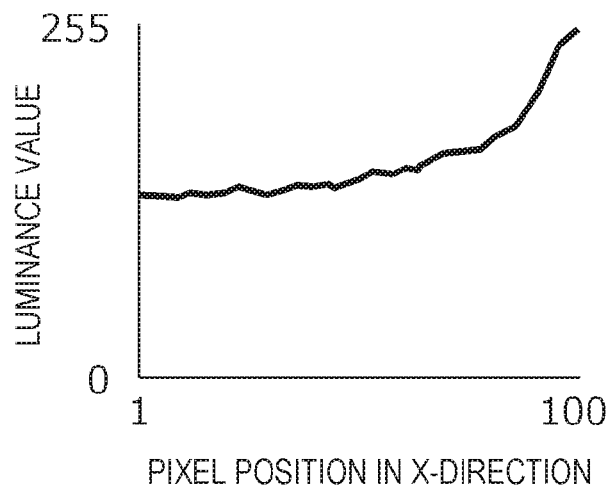
FIG. 7B shows an example of one-dimensional luminance data.
Figure 8A:
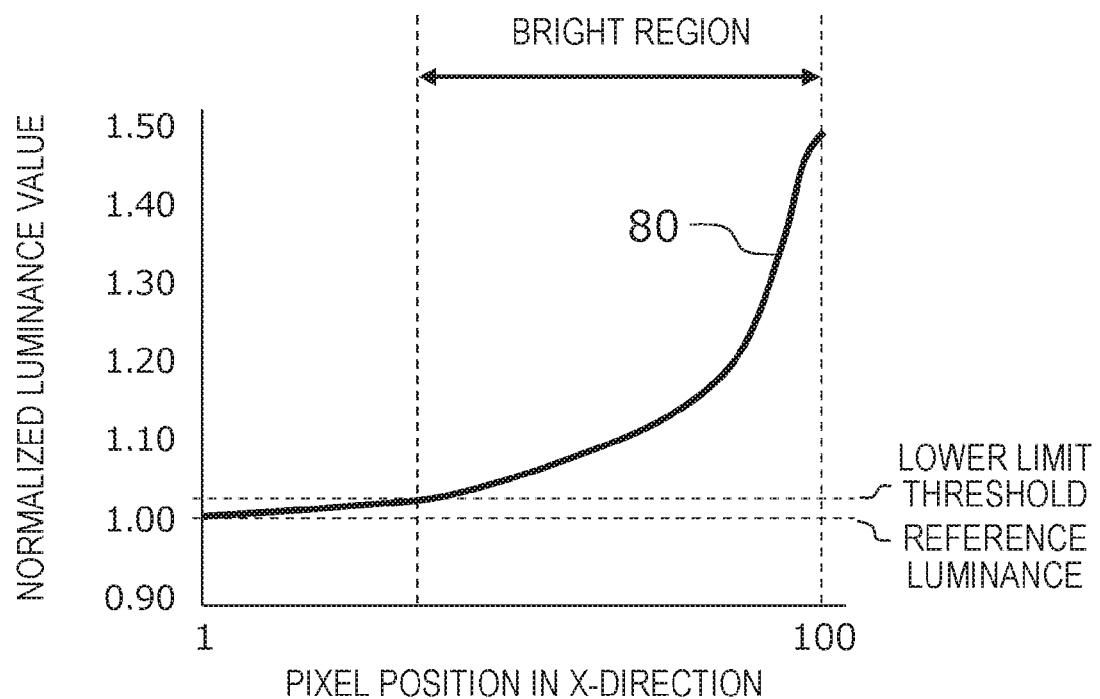
FIG. 8A illustrates an example of normalized luminance data (a luminance profile)

In step S53, the inspecting unit 41 produces a one-dimensional luminance profile which represents change in the luminance value in the X-direction within the inspecting range 62 on the basis of the image in the inspecting range 62. For example, the inspecting unit 41 calculates the average of the luminance values (the pixel values) for each row (which refers to 200 pixels arranged in the Y-direction) of the image within the inspecting range 62, and obtains one-dimensional luminance data (data on the luminance average value for 100 rows). FIG. 7A shows an example of the image within the inspecting range 62, and FIG. 7B shows an example of the one-dimensional luminance data. The abscissa of the graph in FIG. 7B indicates the pixel position in the X-direction within the inspecting range 62, and the ordinate represents the average luminance value. Then, the inspecting unit 41 reduces noises by smoothing the one-dimensional luminance data and normalizes the resulting data by a reference luminance value. The reference luminance value is a luminance value in a region with no bright edge (a normal luminance value). According to the embodiment, a minimum luminance value in the one-dimensional luminance data is used as the reference luminance value. Note however that the reference luminance value may be determined by any other way. For example, a luminance value at the left end (closest to the light source side) in the one-dimensional luminance data may be selected as a reference luminance value or the average value or mode in the entire light-emitting surface image or in a center part thereof may be selected as the reference luminance value. Alternatively, a fixed value preset in the storing unit 43 may be used. FIG. 8A shows an example of the normalized luminance data. The ordinate represents the normalized luminance value when the reference luminance value is 1.0. According to the embodiment, the normalized luminance data is referred to as a luminance profile 80.

In step S54, the inspecting unit 41 detects a bright region from the luminance profile. The bright region is a region which is brighter than a lower limit threshold value in the inspecting range. According to the embodiment, the lower limit threshold value is set to a value which is 1.025 times as large as the reference luminance value, and an X-range having a luminance value exceeding the lower limit threshold value in the luminance profile is detected as a bright region (FIG. 8A). Here, the lower limit threshold is set because luminance unevenness is not noticeable and does not have to be taken into consideration in bright edge evaluation if the luminance difference from the reference luminance value (in other words the luminance value of the surrounding region) is small (not more than the lower limit threshold value).

Figure 8B:
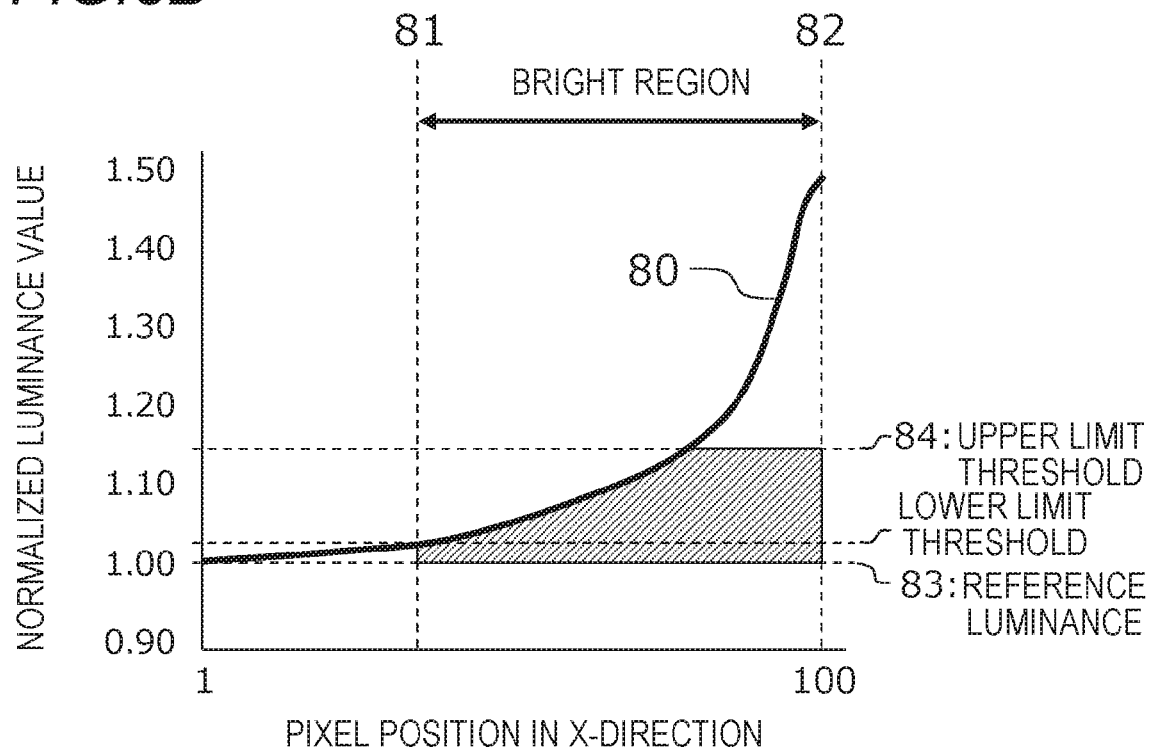
FIG. 8B is a view for illustrating a bright edge evaluation value.

If a bright region is detected in step S54, the process proceeds to step S55, while if no bright region is detected, the process proceeds to step S56. In step S55, the inspecting unit 41 calculates a bright edge evaluation value from the luminance profile of the bright region. More specifically, as shown in FIG. 8B, the inspecting unit 41 calculates the area of a closed region (hatched) 85 by the luminance profile 80 in the bright region, two straight lines 81 and 82 indicating the X-range of the bright region, a straight line 83 indicating the reference luminance value, and a straight line 84 indicating the upper limit threshold value, and obtains the area value as a bright edge evaluation value for the inspecting range.

The lateral width of the closed region 85 corresponds to the size of the bright region, and the longitudinal width of the closed region 85 corresponds to the luminance of the bright region (the luminance difference from the reference luminance value). Therefore, the area value of the closed region 85 corresponds to an evaluation value for evaluating both the size and luminance of the bright region.

Here, the upper limit threshold value is provided for the following reason. The bright edge has a locally extremely bright spot in some cases. In this case, if the luminance of the spot is directly reflected on calculation of a bright edge evaluation value, the evaluation value could be excessive and differ materially from the result of human sensory inspection. In human sensory inspection, luminance exceeding a certain level hardly affects the luminance unevenness evaluation. (In other words, when the luminance exceeds a certain level, a person tends to perceive the luminance unevenness about in the same level regardless of actual luminance values.) Therefore, according to the embodiment, the upper limit threshold value is set so that the influence of the luminance of a part brighter than the upper limit threshold value upon the evaluation value is reduced, so that an appropriate evaluation value (close to that obtained in human sensory inspection) can be obtained even if there is an extremely bright spot. The upper limit threshold value may be set to an appropriate value on the basis of a result of sensory inspection or a result of experiments. According to the embodiment, the upper limit threshold value is set to a value which is 1.15 times as large as the reference luminance value.

It is determined in step S56 whether the inspecting unit 41 has obtained an evaluation value for the entire inspecting range, and if there is a part of the inspecting range yet to be processed, the process returns to step S52, and generation of a luminance profile and calculation of a bright edge evaluation value (steps S53 to S55) is repeated while the inspecting range is shifted by a prescribed pitch (for example 5 mm) in the Y-direction. After the processing from steps S52 to S55 is executed for the entire inspecting range, the process proceeds to step S57.

The inspecting unit 41 selects a maximum value among the bright edge evaluation values in the entire inspecting range as a representative evaluation value (step S57), and compares the representative evaluation value to a determination threshold value (step S58). The determination threshold value is used to determine the presence or absence of a bright edge, and may be predetermined for example on the basis of a result of sensory inspection or a result of experiments. The inspecting unit 41 determines that "there is a bright edge" if the representative evaluation value is greater than the determination threshold value (step S59) and otherwise determines that "there is no bright edge" (step S60).

Figure 9:
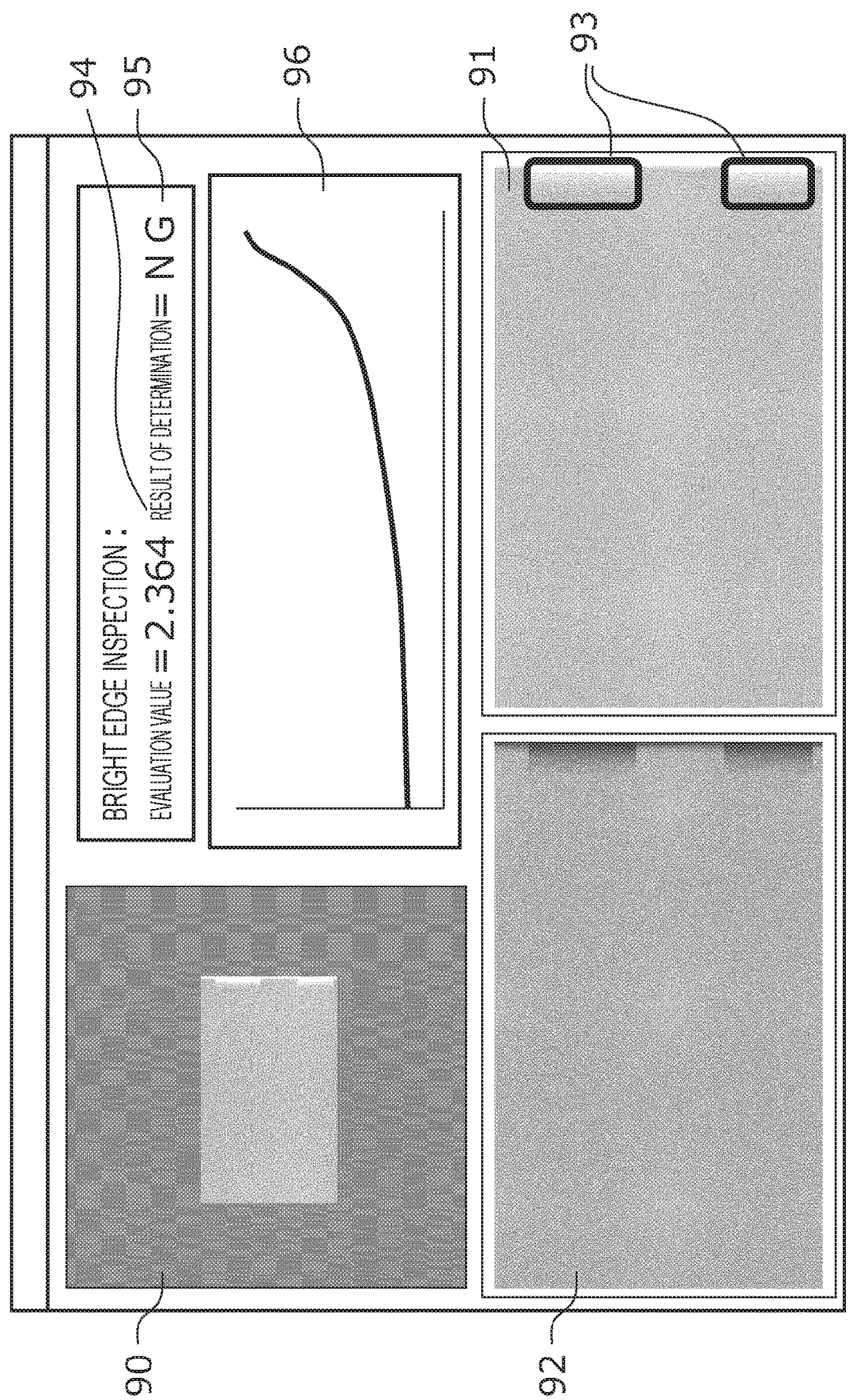
FIG. 9 is a view of an example of an output screen image showing a result of inspection.

In step S61, the output unit 42 produces a screen image for outputting information obtained by the inspecting unit 41 and outputs the screen image to the display device. FIG. 9 illustrates an example of the output screen image about a result of inspection. The output screen image includes an input image 90 taken from the imaging device 31, a light-emitting surface image 91 cut from the input image 90, and an image 92 (such as a pseudo color image) processed to make luminance unevenness more noticeable with respect to the light-emitting surface image 91. The light-emitting surface image 91 is superposed with information 93 indicating a position in which a bright edge appears (for example information indicating the position in which the bright edge evaluation value exceeds the determination threshold value) The screen image also includes a maximum value (a representative evaluation value) 94 for the bright edge evaluation value, its determination result 95, and a luminance profile 96 in the inspecting range in which the representative evaluation value is observed.

Using the inspecting device 3 according to the embodiment, an evaluation value representing the occurrence degree of a bright edge is calculated on the basis of a photographed image of the light-emitting surface of the plane light source device 1, and the presence/absence of a bright edge can be determined on the basis of the evaluation value. Therefore, objective and automatic inspection for bright edges may be performed. Furthermore, since an evaluation value for evaluating both the size and luminance of a bright region is used, a result comparable with the conventional sensory inspection (human visual inspection) can be obtained.

Since the result of inspection shown in FIG. 9 is output, the inspector can immediately determine the presence/absence of a bright edge or whether the plane light source device 1 is good or defective. The bright edge evaluation value is also output, and therefore the reason for the result of determination can be checked, so that convincingness and objectivity about the result of determination may improve. The light-emitting surface image 91 is superposed with the information 93 which indicates the position of a bright edge, which allows the inspector to grasp the position of interest having the bright edge intuitively and easily, which is also useful in checking the actual product. More specifically, the luminance profile 96 is also displayed, so that the size of the bright region and the luminance difference from the reference luminance may be understood.

(Other Matters)

The description of the embodiment is only for the purpose of illustrating the present invention. The invention is not limited by the above specific embodiment, and various modifications can be made within the scope of technical ideas of the invention. For example, in the description of the embodiment, the plane light source device having a rectangular light-emitting surface is illustrated by way of example, while the shape of the light-emitting surface may be any other shape than the rectangular shape. The bright edge evaluation value is only an example, and if the value may be used to evaluate both the size and luminance of a bright region, the value may be designed in any other way. In the inspecting processing shown in FIG. 5, bright edges appearing along a side parallel to the Y-direction of the light-emitting surface image are subjected to inspection, while bright edges appearing along a side parallel to the X-direction as shown in FIG. 2B may be subjected to inspection. In the case, for example, an inspecting range is set along the upper and/or the lower end of the light-emitting surface image, and a bright edge evaluation value may be obtained on the basis of the Y-luminance profile in the inspecting range. It is understood that the bright edge appearing along a side parallel with the Y-direction and the bright edge appearing along a side parallel with the X-direction may both be subjected to inspection. When the side along which a bright edge appears is not parallel with either of the X- and Y-directions or is curved, the inspecting range may be set along the side or the light-emitting surface image may be affine-transformed so that the side becomes a straight line parallel to the X- or Y-direction, and inspection for the bright edge can be carried out by the same method according to the embodiment.

REFERENCE SIGNS LIST

1: Plane light source device
3: Inspecting device,
10: Light-guiding panel,
11: Light source,
20: Bright edge
30: Information processing device,
31: Imaging device,
32: Stage,
33: Constant current power source
40: Image acquiring unit,
41: Inspection unit,
42: Output unit,
43: Storing unit
60: Input image,
61: Light-emitting surface image
80: Luminance profile

The invention claimed is:

1. An inspecting device for inspecting for a failure related to luminance unevenness in a light-emitting surface of a plane light source device, the plane light source device being an edge-lit type plane light source device having a light source arranged along one side of the light-emitting surface, and a light-guiding panel which guides light emitted from the light source to the light-emitting surface, the failure being a part brighter than reference luminance appearing at an end of the light-emitting surface excluding a part provided with the light source, the inspecting device comprising a processor configured to perform operations comprising:

operation as an image acquiring unit, which acquires a light-emitting surface image as a photographed image of the light-emitting surface;

operation as an inspecting unit, which sets an inspecting range in a position of the light-emitting surface image in which the failure may appear, detects, from the inspecting range, a bright region which is brighter than a lower limit threshold value, calculates an evaluation value evaluating both a size and a luminance of the bright region, and determines a presence or an absence of the failure based on the evaluation value; and operation as an output unit, which outputs information obtained by the inspecting unit.

2. The inspecting device according to claim 1, wherein the processor is configured to perform operations such that operation as the inspecting unit comprises operation as the inspecting unit that, in response to the bright region including a part brighter than an upper limit threshold value, evaluates the luminance of the part brighter than the upper limit threshold value as being lower than actual luminance thereof in calculating the evaluation value.

3. The inspecting device according to claim 1, wherein the processor is configured to perform operations such that operation as the inspecting unit comprises operation as the inspecting unit that, in response to the bright region including a part brighter than an upper limit threshold value, evaluates the luminance of the part brighter than the upper limit threshold value as being equal to the upper limit threshold value in calculating the evaluation value.

4. The inspecting device according to claim 2, wherein the light-emitting surface image comprises a rectangular image having a side parallel to a first direction and a side parallel to a second direction, and the processor is configured to perform operations such that operation as the inspecting unit comprises operation as the inspecting unit that, in response to the failure appearing along the side parallel to the second direction generates a one-dimensional luminance profile representing change in a luminance value in the first direction in the inspecting range, detects, as the bright region, a range in the luminance profile in the first direction in which the luminance value exceeds the lower limit threshold value, and calculates, as the evaluation value, an area of a closed region surrounded by the luminance profile in the bright region, two straight lines representing the range of the bright region in the first direction, a straight line representing the reference luminance, and a straight line representing the upper limit threshold value.

5. The inspecting device according to claim 4, wherein the reference luminance comprises a minimum luminance value in the luminance profile of the inspecting range.

6. The inspecting device according to claim 4, wherein the lower limit threshold value comprises a value 1.025 times as large as the reference luminance.

7. The inspecting device according to claim 4, wherein the upper limit threshold value comprises a value 1.15 times as large as the reference luminance.

8. The inspecting device according to claim 4, wherein a width of the inspecting range in the second direction is smaller than a width of the light-emitting surface image in the second direction.

9. The inspecting device according to claim 4, wherein the processor is configured to perform operations such that operation as the output unit comprises operation as the output unit that outputs the evaluation value and a result of determination of the presence or the absence of the failure.

10. The inspecting device according to claim 4, wherein the processor is configured to perform operations such that operation as the output unit comprises operation as the output unit that outputs an image obtained by superposing the light-emitting surface image or an image obtained by processing the light-emitting surface image with information indicating a position in which the failure appears.

11. The inspecting device according to claim 4, wherein the processor is configured to perform operations such that operation as the output unit comprises operation as the output unit that outputs a luminance profile of the inspecting range.

12. An inspecting method for inspecting for a failure related to luminance unevenness in a light-emitting surface of a plane light source device, the plane light source device being an edge-lit type plane light source device having a light source arranged along one side of the light-emitting surface and a light-guiding panel which guides light emitted from the light source to the light-emitting surface,
the failure being a part brighter than reference luminance appearing at an end of the light-emitting surface excluding a part provided with the light source,
the inspecting method comprising:
acquiring a light-emitting surface image as a photographed image of the light-emitting surface;
setting an inspecting range in a position of the light-emitting surface image in which the failure may appear;
detecting, from the inspecting range, a bright region which is brighter than a lower limit threshold value;
calculating an evaluation value evaluating both a size and a luminance of the bright region;
determining a presence or an absence of the failure based on the evaluation value; and
outputting a result of determination of the presence or the absence of the failure.

13. A non-transitory computer readable storage medium storing a program for allowing a computer to execute the inspecting method according to claim 12.

* * * * *